United States Patent
Algawi et al.

(10) Patent No.: US 11,123,903 B2
(45) Date of Patent: Sep. 21, 2021

(54) CONTROLLING BUBBLE FORMATION IN SILICONE FOAM FILLER OF BREAST IMPLANTS

(71) Applicant: Biosense Webster (Israel) Ltd., Yokneam (IL)

(72) Inventors: Yehuda Algawi, Binyamina (IL); Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 294 days.

(21) Appl. No.: 16/170,910

(22) Filed: Oct. 25, 2018

(65) Prior Publication Data
US 2020/0129286 A1 Apr. 30, 2020

(51) Int. Cl.
*B29C 44/18* (2006.01)
*B29C 44/60* (2006.01)
(Continued)

(52) U.S. Cl.
CPC .............. *B29C 44/348* (2013.01); *A61F 2/12* (2013.01); *A61L 27/56* (2013.01); *B29C 44/182* (2013.01); *B29C 44/60* (2013.01); *C08J 9/08* (2013.01); *A61F 2240/001* (2013.01); *A61L 27/18* (2013.01); *B29K 2083/00* (2013.01); *B29L 2031/7532* (2013.01); *C08J 9/30* (2013.01); *C08J 2383/04* (2013.01)

(58) Field of Classification Search
CPC .................. A61F 2240/001; A61F 2/12; B29L 2031/7532; B29C 44/348; B29C 44/182; B29C 44/60; A61L 27/18; A61L 27/56
See application file for complete search history.

(56) References Cited

U.S. PATENT DOCUMENTS

| | | | |
|---|---|---|---|
| 5,605,693 A | | 2/1997 | Seare, Jr. |
| 5,658,330 A | * | 8/1997 | Carlisle ................. A61F 2/0077 623/11.11 |

(Continued)

FOREIGN PATENT DOCUMENTS

| | | | |
|---|---|---|---|
| JP | 4767516 B2 | * | 9/2011 |
| KR | 20080028549 A | * | 4/2008 |

(Continued)

OTHER PUBLICATIONS

PCT/IB2019/059102—International Search Report dated Jun. 25, 2020.

*Primary Examiner* — Joseph S Del Sole
*Assistant Examiner* — Jerzi H Moreno Hernandez
(74) *Attorney, Agent, or Firm* — Eugene L. Szczecina, Jr.

(57) ABSTRACT

A method for manufacturing a breast implant includes producing an elastic filler material including foam, by applying a source of gas bubbles to a silicone monomer to create a mixture. The mixture is inserted into a sealed chamber. After inserting the mixture, a pressure inside the sealed chamber is set to a first pressure, and a temperature of the mixture inside the sealed chamber is set to a first temperature. Then, following a preset time duration, the pressure is lowered to a second pressure that is lower than the first pressure, and after a given time, the temperature is lowered to a second temperature that is lower than the first temperature. A flexible shell, configured for implantation within a breast of a human subject, is filled with the elastic filler material.

4 Claims, 2 Drawing Sheets

(51) Int. Cl.
*B29K 105/00* (2006.01)
*B29C 44/34* (2006.01)
*A61F 2/12* (2006.01)
*C08J 9/08* (2006.01)
*B29K 83/00* (2006.01)
*B29L 31/00* (2006.01)
*A61L 27/56* (2006.01)
*A61L 27/18* (2006.01)
*C08J 9/30* (2006.01)

(56) References Cited

U.S. PATENT DOCUMENTS

| | | | |
|---|---|---|---|
| 2001/0038831 A1 | | 11/2001 | Park et al. |
| 2006/0235094 A1 | * | 10/2006 | Habibi-Naini ...... B29C 44/3446 |
| | | | 521/50 |
| 2008/0215149 A1 | | 9/2008 | Bae |
| 2011/0029077 A1 | | 2/2011 | Choi |
| 2011/0224317 A1 | | 9/2011 | O'Leary |
| 2012/0277860 A1 | | 11/2012 | Dvir et al. |
| 2015/0327985 A1 | * | 11/2015 | Hristov ................. A61B 8/481 |
| | | | 623/8 |
| 2017/0226305 A1 | * | 8/2017 | Katano ................ C08G 65/336 |
| 2019/0314144 A1 | | 10/2019 | Govari et al. |
| 2019/0344480 A1 | * | 11/2019 | Kim ....................... B33Y 80/00 |
| 2019/0358024 A1 | | 11/2019 | Govari et al. |

FOREIGN PATENT DOCUMENTS

| | | | | |
|---|---|---|---|---|
| KR | 20080028549 A | | 4/2008 | |
| KR | 20080095023 A | * | 10/2008 | ............... A61F 2/12 |

\* cited by examiner

CONTROLLING BUBBLE FORMATION IN SILICONE FOAM FILLER OF BREAST IMPLANTS

FIELD OF THE INVENTION

The present invention relates generally to medical implants, and particularly to breast implants.

BACKGROUND OF THE INVENTION

A breast implant may be inserted into a human breast or attached on the breast, e.g., in order to replace tissue that has been medically removed in an operation such as a mastectomy, or for cosmetic purposes. The purpose of the breast implant is to restore to the breast its external form, including its tactile feel and weight.

Various technologies are employed to form breast implants. For example, U.S. Patent Application Publication 2011/0029077 describes a medical implant that includes porous silicon with bubbles of different sizes, and a silicon film enclosing the porous silicon. Also, the medical implant includes porous silicon balls with bubbles and a silicon film enclosing the porous silicon balls. Cushion and weight of the implant can be properly adjusted so as to maintain the cushion at a level similar to that of cellular cells of the human body and to shorten a recovery time. Plural grooves or through-holes are provided on a surface of the implant, and thus body fluid smoothly flows through the grooves or through-holes to improve the affinity of the implant against the cellular cells.

As another example, U.S. Patent Application Publication 2012/0277860 describes a prosthetic implant material for use in a prosthetic implant, comprising a gel and optionally a gas. In an embodiment, the filling material is a mixture of an unrestricted grade of Silicone gel and specially customized hollow glass microspheres filled with a gas.

U.S. Pat. No. 5,658,330 describes a breast prosthesis for implantation beneath the skin. In an embodiment, the prosthesis has an outer elastic shell which encloses a biocompatible fluid and a silicone foam insert of unitary construction having the shape and approximate consistency of breast tissue. The foam insert occupies substantially the entire volume enclosed by the shell of the implantable prosthesis and consists of a foam body that is molded to the shape of the breast. The insert is of unitary construction and is made by (a) heating a mold to an appropriate temperature; (b) mixing air bubbles into a dispersion of uncured silicone; (c) injecting the bubble-laden, uncured silicone into the preheated mold; and (d) applying a vacuum until the foam insert cures.

U.S. Patent Application Publication 2001/0038831 describes forming a super-porous hydrogel composite by polymerizing one or more ethylenic unsaturated monomers, and a multi-olefinic crosslinking agent, in the presence of particles of a disintegrant and a blowing agent. The disintegrant, which rapidly absorbs water, serves to greatly increase the mechanical strength of the super-porous hydrogel and significantly shorten the time required to absorb water and swell. Super-porous hydrogel composites prepared by this method have an average pore size in the range of 10 μm to 3,000 μm. Preferred particles of disintegrant include natural and synthetic charged polymers. The blowing agent is preferably a compound that releases gas bubbles upon acidification, such as $NaHCO_3$. Improved hydrogel composites formed without a blowing agent are also provided.

U.S. Patent Application Publication 2015/0305853 describes a breast implant which includes a filling, or core having a lower overall density relative to silicone gel-filled or saline-filled implant. The core may be a composite including flexible, bodies, for example, air-containing, or gas-containing, bodies, and a gel medium between or around the bodies.

SUMMARY OF THE INVENTION

An embodiment of the present invention provides a method for manufacturing a breast implant, including producing an elastic filler material including foam by applying a source of gas bubbles to a silicone monomer to create a mixture. The mixture is inserted into a sealed chamber. After inserting the mixture, a pressure inside the sealed chamber is set to a first pressure, and a temperature of the mixture inside the sealed chamber is set to a first temperature. Then, following a preset time duration, the pressure is lowered to a second pressure that is lower than the first pressure, and after a given time, the temperature is lowered to a second temperature that is lower than the first temperature. A flexible shell, configured for implantation within a breast of a human subject, is filled with the elastic filler material.

In some embodiments, applying the source of gas bubbles includes mixing a carbonate with the silicone monomer.

In some embodiments, mixing the carbonate includes mixing sodium bicarbonate.

In an embodiment, applying the source of gas bubbles includes flowing pressurized gas into the silicone monomer.

In another embodiment, flowing the pressurized gas includes flowing pressurized air.

In some embodiments, lowering the pressure includes lowering the pressure at a given rate.

In some embodiments, producing the elastic filler material includes producing a foam of silicone gel mixed with the gas bubbles.

In an embodiment, producing the elastic filler material includes tuning a hardness of the silicone gel by tuning at least one property, selected from the group of properties consisting of a size and a density of the gas bubbles.

In another embodiment, producing the foam mixed with the gas bubbles includes producing the foam mixed with carbon dioxide bubbles that are released during production of the foam.

There is additionally provided, in accordance with an embodiment of the present invention, an apparatus for manufacturing an elastic filler material including foam, the apparatus including a sealed chamber and a controller. The sealed chamber is configured to hold a mixture of a source of gas bubbles and a silicone monomer under controlled temperature and pressure. The controller is configured to produce the elastic filler material including the foam, by, after inserting the mixture into the sealed chamber, setting (i) a pressure inside the sealed chamber to a first pressure, and (ii) a temperature of the mixture inside the sealed chamber to a first temperature, and then, following a preset time duration, (i) lowering the pressure to a second pressure that is lower than the first pressure, and (ii) after a given time, lowering the temperature to a second temperature that is lower than the first temperature.

The present invention will be more fully understood from the following detailed description of the embodiments thereof, taken together with the drawings in which:

DETAILED DESCRIPTION OF EMBODIMENTS

Overview

Figure 1:
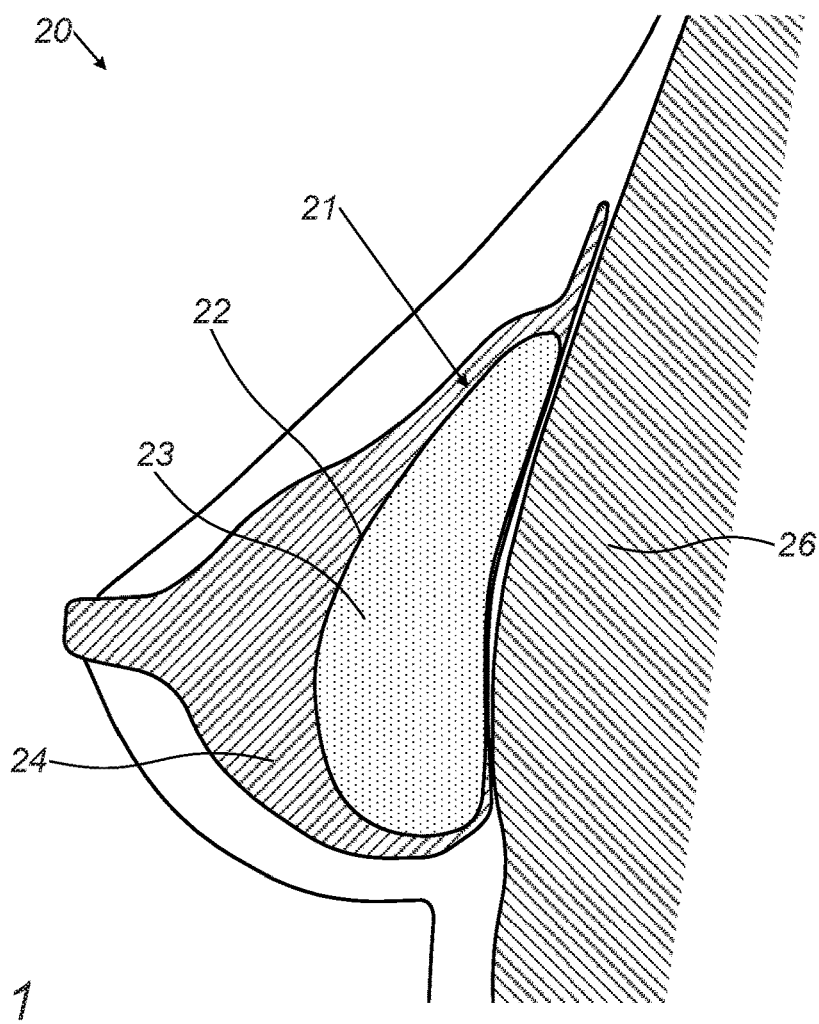
FIG. 1 is a schematic, sectional illustration of a human female breast with a breast implant, in accordance with an embodiment of the invention.

A breast implant may contain an elastic filler material, such as silicone gel, which is contained in a sealed flexible shell. A breast implant filled with such a material, however, would be relatively heavy and may cause discomfort to the wearer of the implant.

Embodiments of the present invention that are described hereinafter provide manufacturing methods and an apparatus for producing homogeneous silicon foam to produce light-weight breast implant. In some embodiments, a source of gas bubbles is either applied to (e.g., mixed with) a silicone monomer to create a mixture that, using the disclosed methods and apparatus of manufacturing, produces the foam comprising the gas bubbles. In an embodiment, a gas, such as air or nitrogen, is injected into an uncured silicone monomer liquid, to create a mixture that is further processed into the foam, as described below. In another embodiment, carbon dioxide is generated in the silicone gel to form the foam by a chemical reaction, wherein the bubbles in the foam comprise chiefly the carbon dioxide gas.

A method for chemically preparing silicone foam comprising carbon dioxide gas by mixing sodium bicarbonate with hydrolyzed uncured silicone monomer liquid is described in U.S. Provisional Patent Application 62/658, 896, filed Apr. 17, 2018, entitled "Reducing Breast Implant Weight Using Chemically Produced Foam Filling," which is assigned to the assignee of the present patent application and whose disclosure is incorporated herein by reference.

Regardless of the manner in which the gas bubbles are realized in the silicone monomer, the resulting mixture should be heated so as to polymerize the silicone. Furthermore, the heating causes, for example, the sodium bicarbonate to decompose and release more carbon dioxide bubbles. If gas, such as air, is injected, the heating causes gas bubbles to form within the silicone as it cures, which results in the formation of a stable silicone foam.

Producing the silicone foam by either of the two methods described above can be relatively complicated if there is no control over the timing of the release of the gas bubbles. An uncontrolled manufacturing process may result in the bubbles being released before the silicone has completely cured, and thereby cause the formation of an inhomogeneous elastic filler material (e.g., as separated volumes of silicone and gas).

In some embodiments, a silicone foam is produced by first mixing sodium bicarbonate with the silicone monomer and inserting the mixture into a sealable chamber. Next, a controller directs a pressure control machinery that is connected to the chamber via one or more pipes and valves, to set a pressure inside the sealed chamber to a first pressure. In some embodiments, the controller directs the machinery to increase the pressure in the sealed chamber by a preset value of up to one atmosphere. In general, the controller and the pressure control machinery are configured to modify the pressure inside the sealed chamber (i.e., raise, lower, or equalize the pressure relative to the ambient atmospheric pressure).

After pressurizing the chamber, the controller, which further controls controllable electrical heater, directs the controllable electrical heater to raise the temperature of the mixture inside the sealed chamber to a first temperature. In some embodiments, the temperature of the chamber is raised to a preset high temperature value, which is sufficiently high for a curing process of the silicone monomer to commence.

At a proper timing during the curing process (e.g., after a preset time determined be by trial and error. the controller directs the pressure-controlled machinery to lower the pressure to a second pressure that is lower than the first pressure. For example, the controller directs the machinery to gradually releases the pressure to the ambient atmospheric level by, for example, gradually releasing pressurized gases inside the chamber into the ambient atmosphere via a venting line having a valve. The gradual release of pressure permits the dissolved carbon dioxide in the curing mixture to form bubbles which are trapped in the cured silicone in such way that it forms homogeneous silicone foam (i.e., regulates the timing and rate of bubble release to best match the curing process). Typically, the initial pressure is set to about one Atm over ambient pressure, wherein the low pressure, as well the pressure reduction rate, are set by trial and error (i.e., optimized empirically).

In some embodiments, at a proper timing during the curing process, the controller directs the pressure control machinery to evacuate the chamber to a second pressure that is low pressure (i.e., below the ambient atmospheric pressure), so as to stimulate, for example, the generation of the gas bubbles. Correspondingly, such evacuation may achieve a less dense foam.

A given time after pressure was lowered, the controller directs the controllable electrical heater to stop the heating and the chamber typically slowly cools to room temperature.

In an embodiment, the elasticity of the foam is tuned during production by regulating the size and/or density of the trapped carbon dioxide bubbles, for example, by the timing and/or rate of pressure adjustments. The elasticity (e.g., hardness) of the foam may be determined in the development stage of the gel preparation process, for example by trial and error, and kept the same by a stable manufacturing process.

In another embodiment, the silicone foam filling of the implant is produced by first mixing air into the silicone monomer. The tooling for the mixing process (e.g., a nozzle that flows compressed air into the silicone and a spinner homogenizing the resulting mixture) generates very small air bubbles that are homogeneously suspended in the mixture (causing the liquid mixture to appear white). The bubble size is determined by the mixing speed, where a higher speed produces smaller bubbles and a lower speed produces larger bubbles.

Alternatively or additionally, some of the mixed air may actually dissolve in the silicone monomer liquid. The mixture is then inserted into the sealed chamber for further processing, where the rest of the production steps are similar to those described above. Again, the homogeneity, density, and degree of elasticity of the foam is tuned during production by regulating the size and/or density of the trapped air bubbles, for example, by the timing and/or rate of pressure adjustment.

In some embodiments, a breast implant is further provided, which comprises one of the disclosed foams and a flexible shell that is configured to contain the foam and is further configured for implantation within a breast of a human subject. The disclosed method comprises filling the flexible shell with the elastic filler material, for example, by injecting one of the disclosed foams.

The disclosed technique for preparing silicone foam as described above, implementing either method for producing the initial mixture (mixing sodium bicarbonate or injecting air) and by controlling the curing process in a sealed chamber, can simplify the formation of light breast implants. Thus, implementing the disclosed technique may increase the availability of light breast implants.

System Description

FIG. 1 is a schematic sectional illustration of a human female breast 20 with a breast implant 21, in accordance with an embodiment of the present invention. Implant 21 comprises a shell 22 filled with a light-weight foam 23, whereas the foam preparation is described in more detail below. In the disclosed embodiment, breast implant 21 is positioned as a sub-glandular implant between breast tissue 24 and a pectoralis major muscle 26. In alternative embodiments, breast implant 21 may be positioned either as a sub-fascial, sub-pectoral, or sub-muscular implant, referring to different positions of the implant relative to pectoralis major muscle 26, as will be understood by those skilled in the art. The example shown in FIG. 1 is thus chosen purely for the sake of conceptual clarity. Embodiments of the present invention may apply to any design of breast implant that contain a foam.

Controlling Bubble Formation in Silicone Foam Filler of Breast Implants

Figure 2:
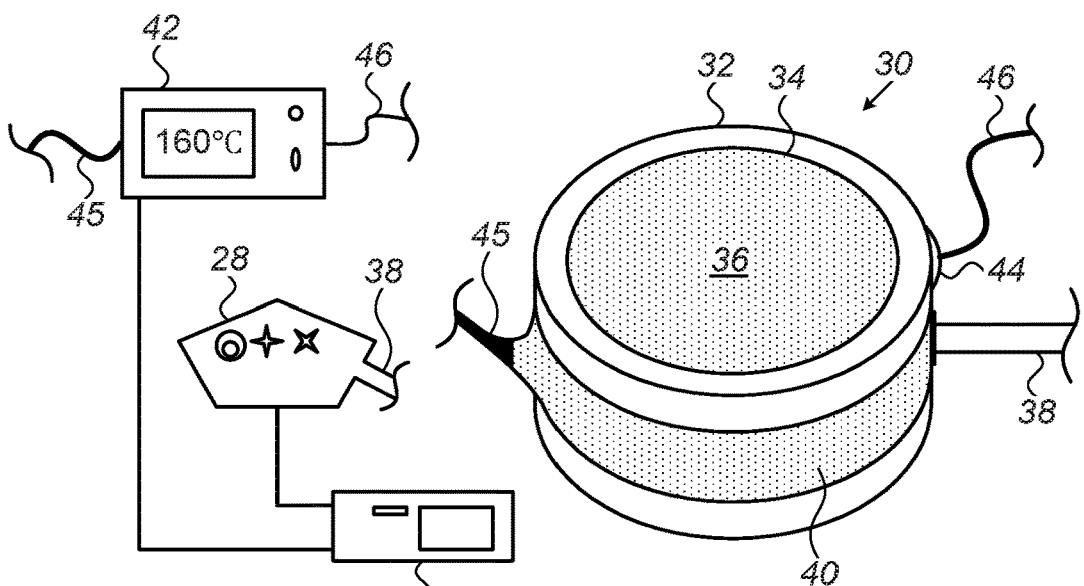
FIG. 2 is schematic, pictorial illustration of an apparatus for producing silicone foam, in accordance with an embodiment of the present invention.

FIG. 2 is schematic, pictorial illustration of an apparatus for producing silicone foam, in accordance with an embodiment of the present invention. As seen, the apparatus comprises a curing chamber 30, which is configured to maintain a manufacturing environment with adjustable pressure and temperature. A removable lid 32 allows a user to insert (e.g., pour) a mixture 36 of, for example, sodium bicarbonate and silicone monomer, into chamber 30. After mixture 36 is in chamber, lid 32 is put back in place to seal chamber 30.

A controller 100 is configured to control pressure control machinery 28 and controllable electrical heater 42. Machinery 28 is connected to the chamber via one or more pipes and valves. To manufacture foam, controller 100 directs machinery 28 to increase the pressure in the sealed chamber by a preset value of typically up to one atmosphere. In response, pressure control machinery 28 (e.g., comprising a compressor) raises the pressure inside chamber 30 via a pipe 38, by the required amount, i.e., by between half a bar and a bar.

After pressure was raised to the first pressure value, the temperature of the mixture is raised to a first temperature value. In an embodiment, controller 100 is configured to direct controllable electrical heater 42 to raise the temperature of the mixture inside the sealed chamber to about 160° C., in order to cure the silicone monomer. The temperature inside chamber 30 is increased using a heater 40, which is coupled to the wall of chamber 30 and is fed with electrical current from controllable electrical heater 42, via cable 45. Controllable electrical heater maintains the preset first temperature based on an indication received from a thermocouple 44 connected to the chamber 30 wall, via wire 46.

Removable lid 32 is fitted with a transparent window 34, which allows a user to observe and evaluate the bubble formation process. For example, the user can see bubble formation as the temperature is raised, and then correspondingly set the timing and duration of a subsequent pressure release step, so as to obtain a required foam texture. In an embodiment, at a proper timing during the curing process, controller 100 directs machinery 28 to evacuate the sealed chamber to establish low pressure that may be lower than a preset second pressure (e.g., a partial vacuum), so as to further enhance bubble formation, so as to manufacture, for example, a lighter foam. To evacuate the chamber, machinery, such as a vacuum pump (not shown), is connected by valves (not shown) via pipe 38 to chamber 30. In alternative embodiment, pressure control machinery 28 lets the pressure return to atmospheric pressure, e.g., by opening a vent as directed by controller 100.

After it was determined that the curing processes has ended, for example, by a user or automatically by a monitoring device, controller 100 directs controllable heater 42 to stop the heating and the chamber slowly cools to room temperature. Subsequently, the user opens lid 32 to take out the ready silicon foam.

The apparatus shown in FIG. 2 is chosen purely for the sake of conceptual clarity. For example, instead of having removable lid 32, chamber 30 may be fitted with a subsystem comprising pumps, pipes, and valves, which is configured to pump raw mixtures into chamber 30 and pump out ready foam. The chamber temperature may be lowered to a preset low temperature by actively cooling the chamber. In an optional embodiment, controller 100 directs a controllable valve of a gas cylinder to open so that the gas flows from the cylinder into chamber 30, via pipe 38, and pressurizes chamber 30. A pressure sensor indicates to processor 100 when a target first pressure inside chamber 30 is achieved. Alternatively, the controllable valve includes a pressure regulator set to the target first pressure.

Figure 3:
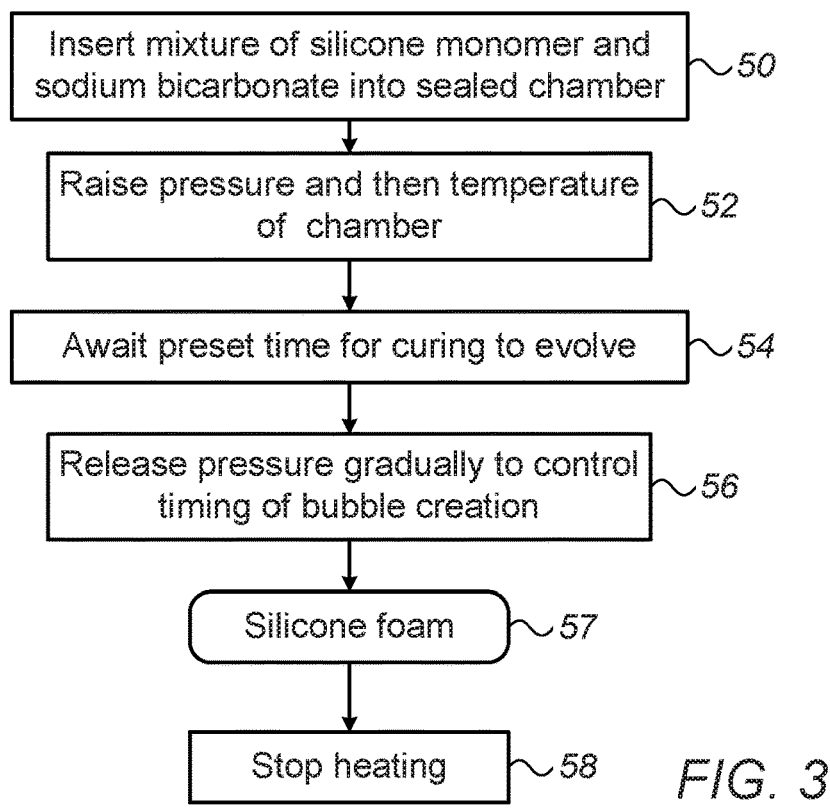
FIG. 3 is a flow chart that schematically illustrates a method for producing silicone foam filling for a breast implant, in accordance with an embodiment of the present invention.

FIG. 3 is a flow chart that schematically illustrates a method for producing silicone foam filling for a breast implant, in accordance with an embodiment of the present invention. The process begins with a user pouring liquid mixture 36, comprising sodium bicarbonate and silicone monomer, into chamber 30, at a mixture poring step 50. Next, the controller 100 directs machinery 28 and controllable heater 42 to raise the pressure and the temperature inside chamber 30, respectively, to establish conditions for silicone curing and carbon dioxide bubble formation, at a conditioning step 52. At a curing step 54, controller 100 awaits a preset time, typically measured in several minutes, for the silicone foam to start forming. Once the silicone foam formation is at a proper stage, as, for example, determined by a user or a monitoring device, controller 100 directs machinery 28 to gradually release the pressure, or evacuates the chamber to achieve partial vacuum, at a pressure release step 56, so as to have the foam produced as required (i.e., to control bubble formation). A resulting silicon foam 57 fills the chamber. A given time after the pressure was released, controller 100 directs heater 42 to stop the heating, at a cool down step 58. The resulting silicon foam can now be removed from the chamber once chamber 30 has cooled.

Figure 4:
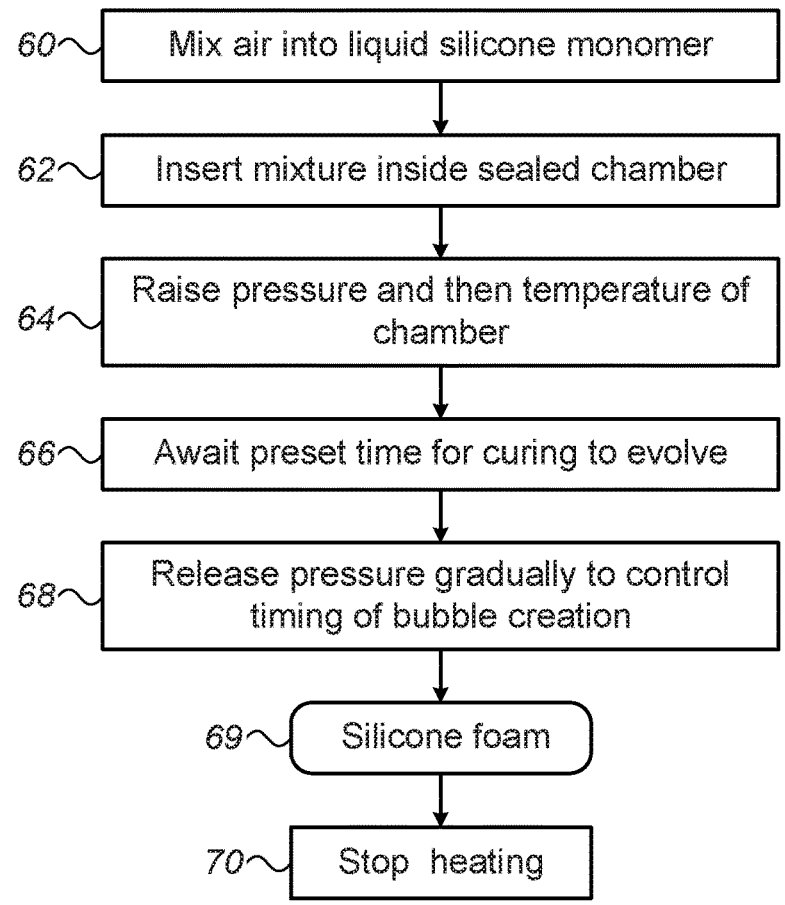
FIG. 4 is a flow chart that schematically illustrates another method for producing silicone foam filling for a breast implant, in accordance with another embodiment of the present invention.

FIG. 4 is a flow chart that schematically illustrates another method for producing silicone foam filling for a breast implant, in accordance with another embodiment of the present invention. The process begins with a user mixing air into a liquid silicone monomer to create a mixture 36, at a mixture preparation step 60. The rest of the process follows that described in FIG. 3. The user pours liquid mixture 36 comprising air and silicone monomer into chamber 30, at a mixture pouring step 62. Next, controller 100 directs machinery 28 and controllable heater 42, respectively, to raise the pressure and the temperature inside chamber 30, to establish conditions for silicone curing and air bubble formation, at a conditioning step 64. At a curing step 66, the user awaits a preset time, typically about five minutes, for the silicone foam to start forming. Once the silicone foam formation is at a proper stage, controller 100 directs machinery 28 to gradually release the pressure, or evacuates the chamber to achieve partial vacuum, at a pressure release step 68, so as to have the foam produced as required. A resulting silicon foam 69 fills the chamber. A given time after the pressure was lowered, controller 100 directs heater 42 to stop the heating, at a cool down step 70. The resulting silicon foam can be removed from the chamber once chamber 30 has cooled.

In some embodiments, a flexible shell is filled with the filling material produced by chamber 30 (using one of the disclosed methods to produce either filling material foam 58 or filling material foam 70), and the shell is then sealed to produce breast implant 21.

The flow charts shown in FIGS. 3 and 4 are chosen purely for the sake of conceptual clarity. The disclosed processes may, for example, be automated, so that there is no need for a user to either manually operate the process as described, or to visually inspect the quality of the foam as it forms. Additionally, the quantities of chemicals and/or the conditions at which the processes produce the bubbles may vary, so as to tune the size and/or density of the chemically resulting gas bubbles in the foam, and the variation in bubble size.

Other manufacturing steps may be included, such as, for example, filtration of one or more of the materials. The timing and duration of manufacturing steps, for example, the curing process, may vary.

Although the embodiments described herein mainly address breast implants, the methods and systems described herein can also be used in other applications, in which an implant comprising silicone-gel needs to be lightweight.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for manufacturing a breast implant, the method comprising: producing an elastic filler material comprising a foam of silicone comprising carbon dioxide bubbles, by:
    applying a source of gas bubbles to a silicone monomer to create a mixture;
    inserting the mixture into a sealed chamber;
    after inserting the mixture, (i) raising pressure inside the sealed chamber to a first pressure, the first pressure being above and up to one atmosphere over ambient pressure and (ii) setting a temperature of the mixture inside the sealed chamber to a first temperature after the pressure is raised to the first pressure to allow silicone curing and carbon dioxide bubble formation; and
    after the mixture is subjected to the first pressure and the first temperature for a preset time duration, (i) lowering the pressure to a second pressure that is lower than the first pressure and (ii) lowering the temperature to a second temperature that is lower than the first temperature after a given time of reaching the second pressure; and
filling with the elastic filler material a flexible shell, the flexible shell being configured for implantation within a breast of a human subject,
wherein applying the source of gas bubbles comprises mixing a carbonate with the silicone monomer, and
wherein the carbonate comprises sodium bicarbonate.

2. The method according to claim 1, wherein lowering the pressure comprises lowering the pressure at a given rate.

3. The method according to claim 1, wherein the foam of silicone is a silicone gel, and the carbon dioxide bubbles are mixed within the silicone gel.

4. The method according to claim 3, wherein producing the elastic filler material comprises tuning a hardness of the silicone gel by tuning at least one property, selected from the group of properties consisting of a size and a density of the carbon dioxide bubbles.

\* \* \* \* \*